(12) United States Patent
Bonneh et al.

(10) Patent No.: US 10,568,557 B2
(45) Date of Patent: Feb. 25, 2020

(54) SYSTEM AND METHOD FOR ANALYZING INVOLUNTARY EYE MOVEMENTS OF A HUMAN SUBJECT IN RESPONSE TO A MASKED VISUAL STIMULATING CONTENT

(71) Applicants: Yoram Bonneh, Hod-Hasharon (IL); Gal Rosenzweig, Kiryat Ono (IL)

(72) Inventors: Yoram Bonneh, Hod-Hasharon (IL); Gal Rosenzweig, Kiryat Ono (IL)

( * ) Notice: Subject to any disclaimer, the term of this patent is extended or adjusted under 35 U.S.C. 154(b) by 54 days.

(21) Appl. No.: 15/898,806

(22) Filed: Feb. 19, 2018

(65) Prior Publication Data
US 2019/0254580 A1    Aug. 22, 2019

(51) Int. Cl.
*A61B 5/16* (2006.01)
*A61B 5/11* (2006.01)
*A61B 3/113* (2006.01)
*A61B 3/00* (2006.01)

(52) U.S. Cl.
CPC ............ *A61B 5/163* (2017.08); *A61B 3/0058* (2013.01); *A61B 3/113* (2013.01); *A61B 5/1103* (2013.01)

(58) Field of Classification Search
CPC ....... A61B 3/0033; A61B 5/162; A61B 5/163; A61B 3/0025; A61B 3/0041; A61B 3/0058; A61B 3/113; A61B 5/1103
USPC ........................................................ 351/209
See application file for complete search history.

(56) References Cited

U.S. PATENT DOCUMENTS

| | | | | |
|---|---|---|---|---|
| 2003/0085894 | A1* | 5/2003 | Tatsumi | G06T 15/506 345/426 |
| 2005/0198316 | A1* | 9/2005 | Gold | G06Q 30/02 709/228 |
| 2010/0010317 | A1* | 1/2010 | De Lemos | A61B 3/113 600/300 |
| 2016/0271002 | A9 | 9/2016 | Simmons | |
| 2017/0281067 | A1* | 10/2017 | Hanina | A61B 3/032 |
| 2017/0300930 | A1 | 10/2017 | Forbes | |
| 2017/0365101 | A1* | 12/2017 | Samec | G02B 27/017 |

OTHER PUBLICATIONS

International Search Report dated Jul. 12, 2019 for corresponding PCT Application No. PCT/IL2019/050195.

* cited by examiner

*Primary Examiner* — Jordan M Schwartz
(74) *Attorney, Agent, or Firm* — Pearl Cohen Zedek Latzer Baratz LLP

(57) ABSTRACT

Methods and systems for analyzing involuntary eye movements of a human subject are disclosed. The systems may include means for presenting to the human subject visual content, possibly a video footage, in which some visual stimulus with whom the human subject has some form of relationship on a cognitive or sentiment level is embedded. The generation of the combined video footage is such that the stimulus is briefly presented and masked by the following video footage. The duration of the stimulus is made sufficiently long to invoke a neural response beyond a specified threshold that generates respective ocular effect, and sufficiently short to prevent a controlled eye movement by the human subject. Once measured, the involuntary eye movements are analyzed in view of the respective stimulating portions—e.g., their timing and context, to yield an analysis of the human subject relationship towards the objects presented in the visual stimulating portions.

14 Claims, 10 Drawing Sheets

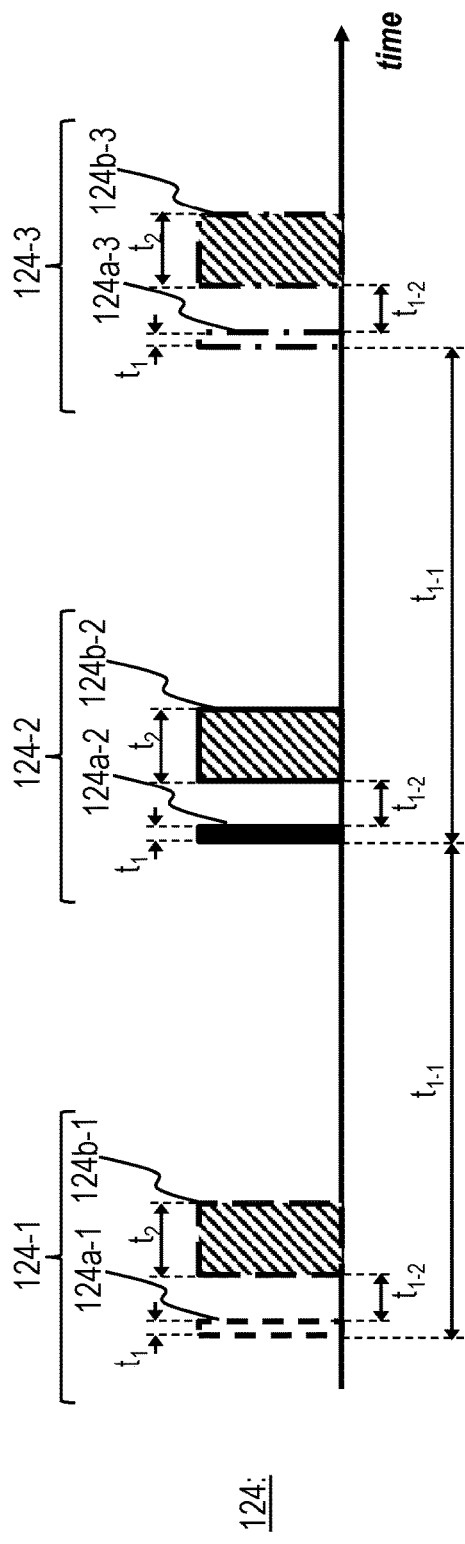
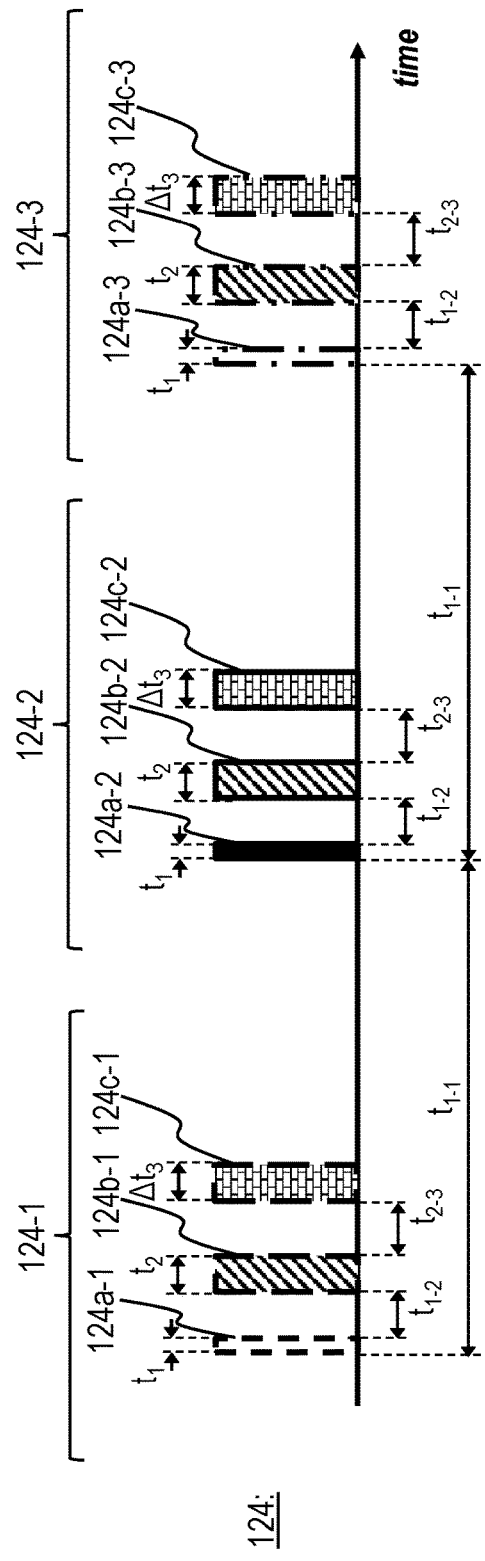
Figure 2A
Figure 2B

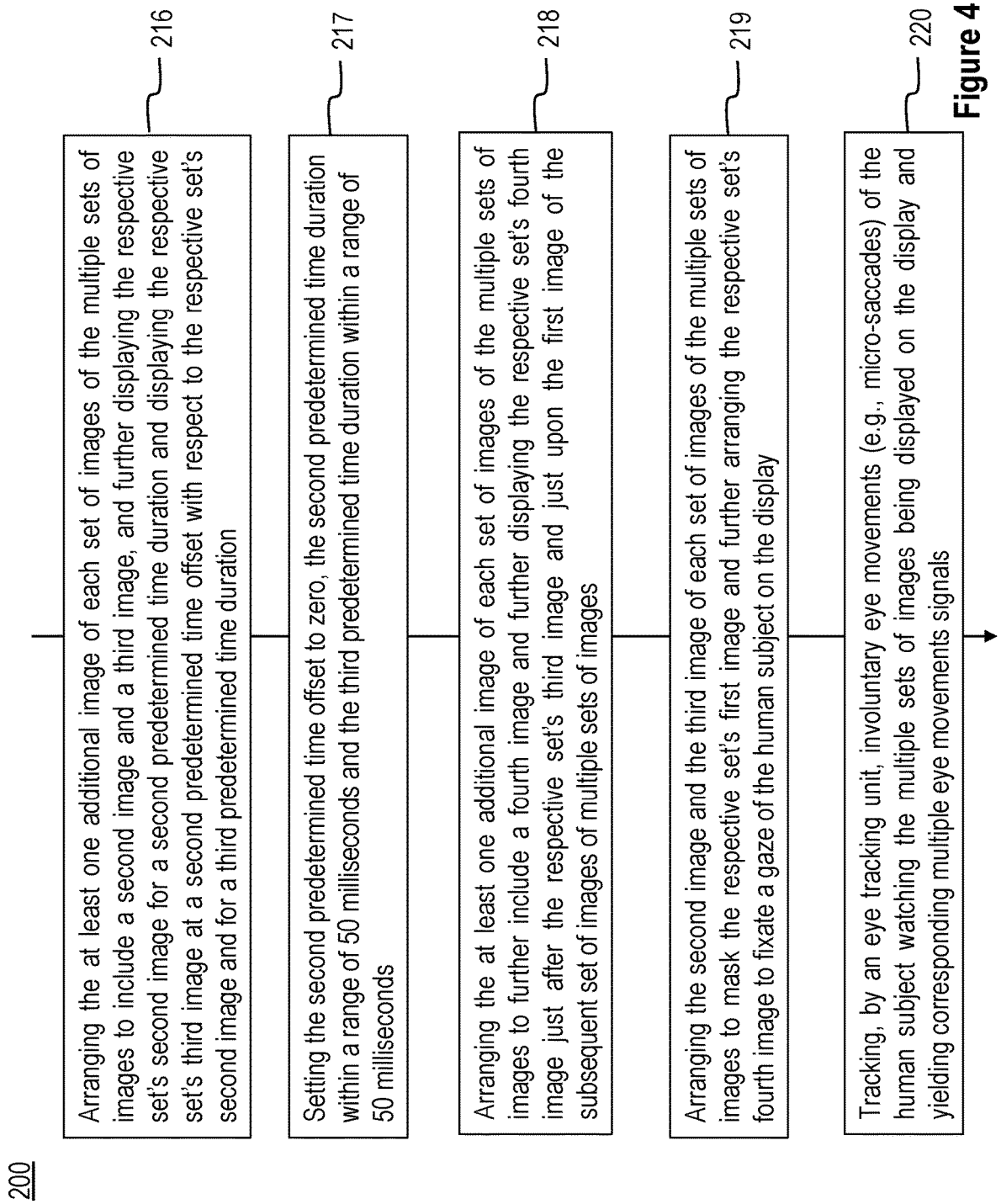
Figure 4 (cont. 1)

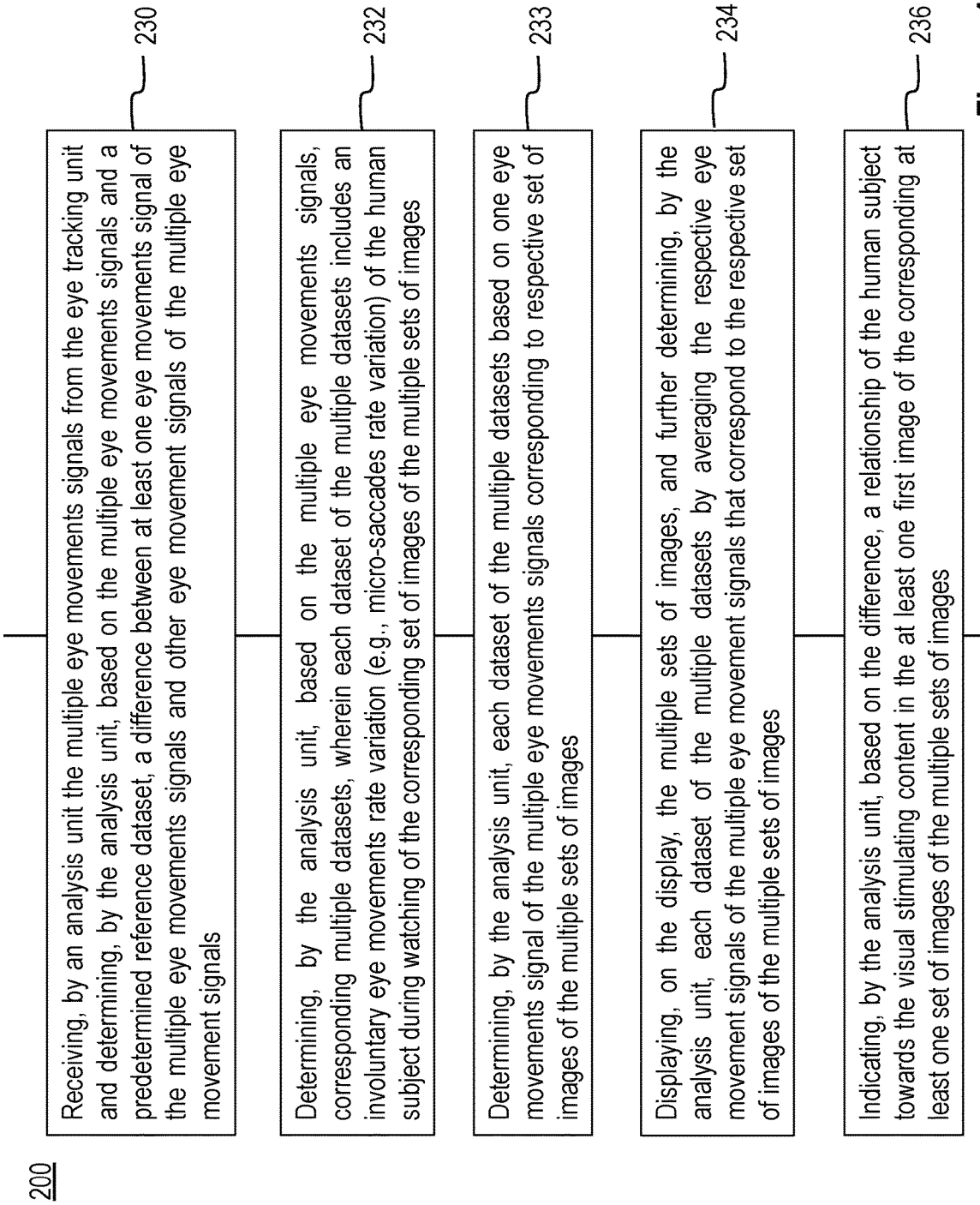

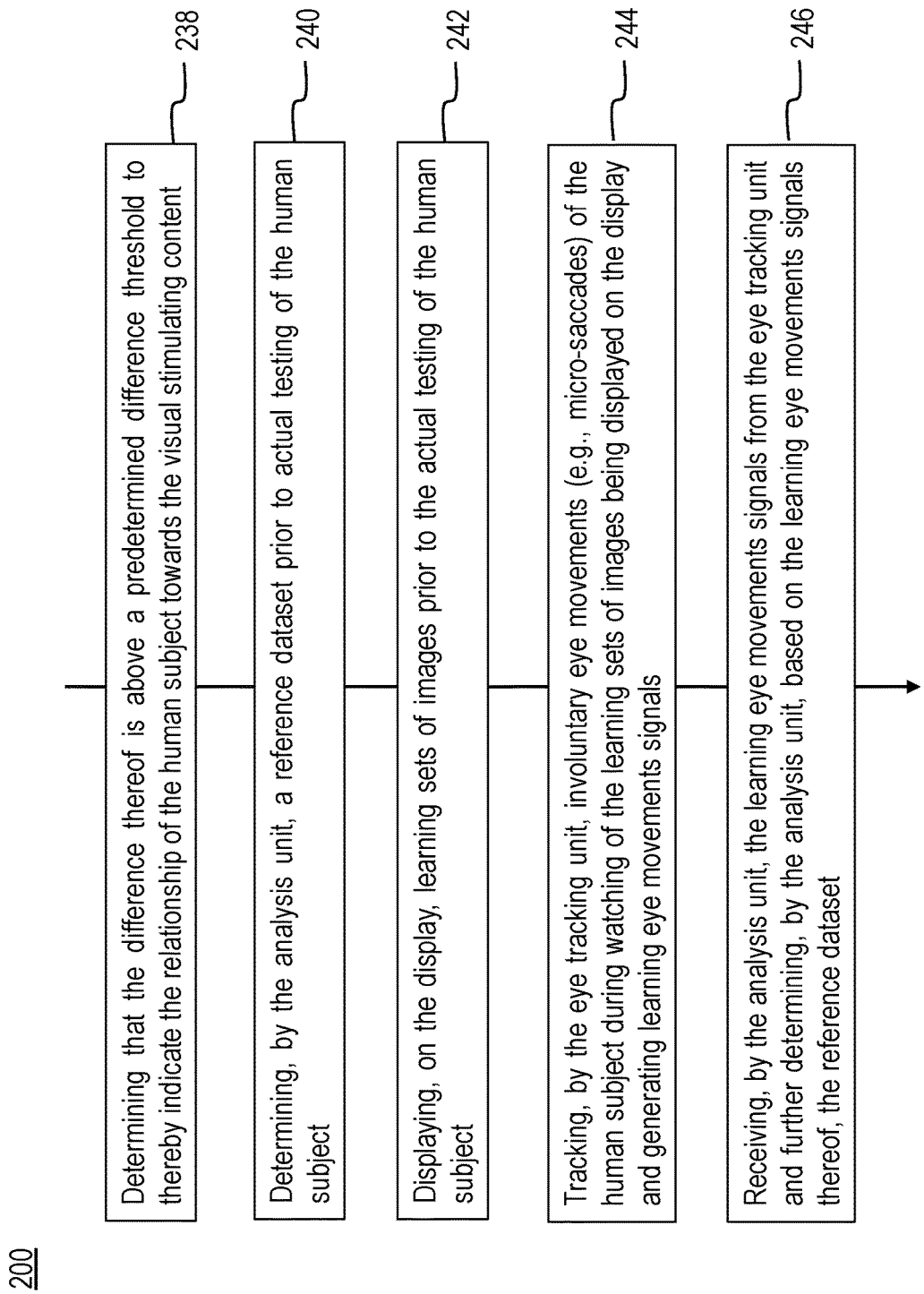
Figure 4 (cont. 3)

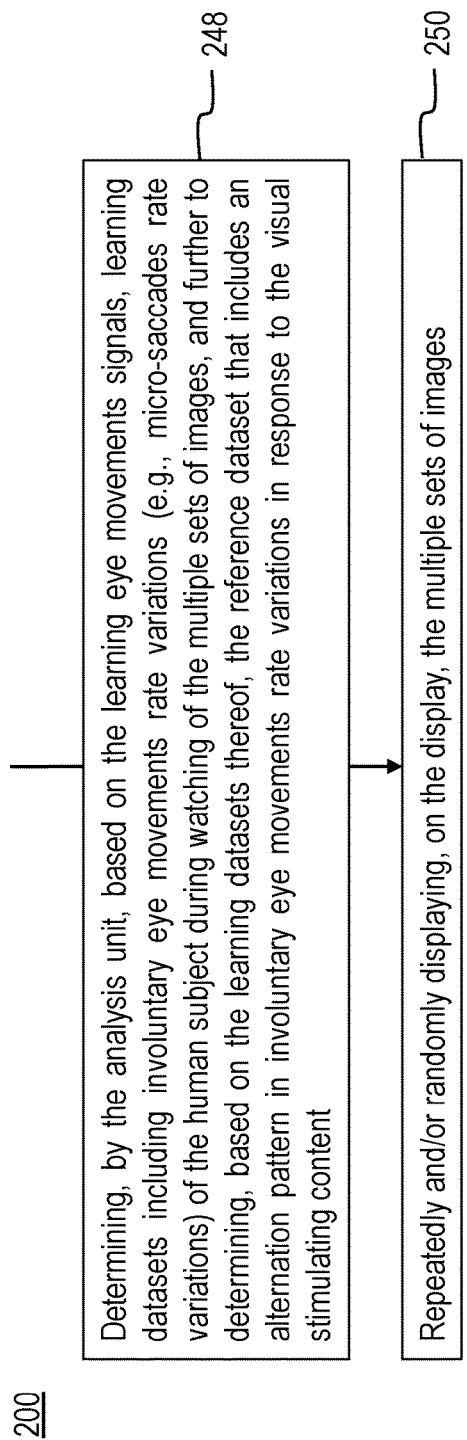
Figure 4 (cont. 4)

US 10,568,557 B2

SYSTEM AND METHOD FOR ANALYZING INVOLUNTARY EYE MOVEMENTS OF A HUMAN SUBJECT IN RESPONSE TO A MASKED VISUAL STIMULATING CONTENT

FIELD OF THE INVENTION

The present invention relates to the field of involuntary eye movement analysis, and more particularly to systems and methods for analyzing involuntary eye movements of a human subject in response to a masked visual stimulating content.

BACKGROUND OF THE INVENTION

Some current methods of indicating a relationship of a human subject towards a visual stimulating content typically require invasive measuring and further analysis of brain activity. Examples of such methods may include CIT test, GAT test, brain fingerprinting test and/or polygraph.

Other current methods of indicating relationship of the human subject towards a visual stimulating content may include noninvasive measuring and further analysis of eye movements of the human subject in response to visual stimulating content. However, these current methods typically suffer from relatively low sensitivity (e.g., as compared to the invasive methods discussed above), as these methods typically utilize visual content presentation protocols that enable the human subject to deceive the test results.

SUMMARY OF THE INVENTION

One aspect of the present invention provides a system for analyzing involuntary eye movements of a human subject in response to a masked visual stimulating content, the system including: a display; a database comprising multiple sets of images, wherein each set of images of the multiple sets of images comprises a first image and at least one additional image displayed after the respective set's first image to thereby mask the respective set's first image, and wherein at least one first image of corresponding at least one set of images of the multiple sets of images comprises a visual stimulating content; a controller in association with the display and with the database, the controller being arranged to display, on the display, the multiple sets of images such that the first images of each two subsequent sets of images of the multiple sets of images are displayed at a second predetermined time offset with respect to each other ranging between 0.5 and 1.5 seconds; an eye tracking unit arranged to track involuntary eye movements of the human subject watching the multiple sets of images being displayed on the display to yield corresponding multiple eye movements signals; and an analysis unit arranged to receive, from the eye tracking unit, the multiple eye movements signals and to determine, based on the multiple eye movements signals and a predetermined reference dataset, a difference between at least one eye movements signal of the multiple eye movements signals and other eye movements signals of the multiple eye movements signals, wherein the difference thereof is due to at least one of a subconscious response or a response on a verge of consciousness of the human subject to the visual stimulating content presented in the corresponding at least one first image of the corresponding at least one set of images of the multiple sets of images.

Another aspect of the present invention provides a method of analyzing eye movements of a human subject in response to a masked visual stimulating content, the method including: displaying, on a display, multiple sets of images, wherein each set of images of the multiple sets of images comprises a first image and at least one additional image being displayed after the first image to thereby mask the first image, wherein at least one first image of corresponding at least one set of images of the multiple sets of images comprises a visual stimulating content, and wherein each two subsequent sets of images of the multiple sets of images are displayed at a second predetermined time offset with respect to each other ranging between 0.5 and 1.5 seconds; tracking, by an eye tracking unit, involuntary eye movements of the human subject watching the multiple sets of images being displayed on the display and yielding corresponding multiple eye movements signals; receiving, by an analysis unit, the multiple eye movements signals from the eye tracking unit and determining, by the analysis unit, based on the multiple eye movements signals and a predetermined reference dataset, a difference between at least one eye movements signal of the multiple eye movements signals and other eye movements signals of the multiple eye movements signals, wherein the difference thereof is due to at least one of a subconscious response or a response on a verge of consciousness of the human subject to the visual stimulating content presented in the corresponding at least one first image of the corresponding at least one set of images of the multiple sets of images.

These, additional, and/or other aspects and/or advantages of the present invention are set forth in the detailed description which follows, possibly inferable from the detailed description, and/or learnable by practice of the present invention.

BRIEF DESCRIPTION OF THE DRAWINGS

For a better understanding of embodiments of the invention and to show how the same can be carried into effect, reference will now be made, purely by way of example, to the accompanying drawings in which like numerals designate corresponding elements or sections throughout.

In the accompanying drawings:

FIG. 2A-2D are graphs of various configurations of multiple sets of images being displayed on a display of a system for analyzing involuntary eye movements of a human subject in response to a masked visual stimulating content, according to some embodiments of the invention;

Figure 1:
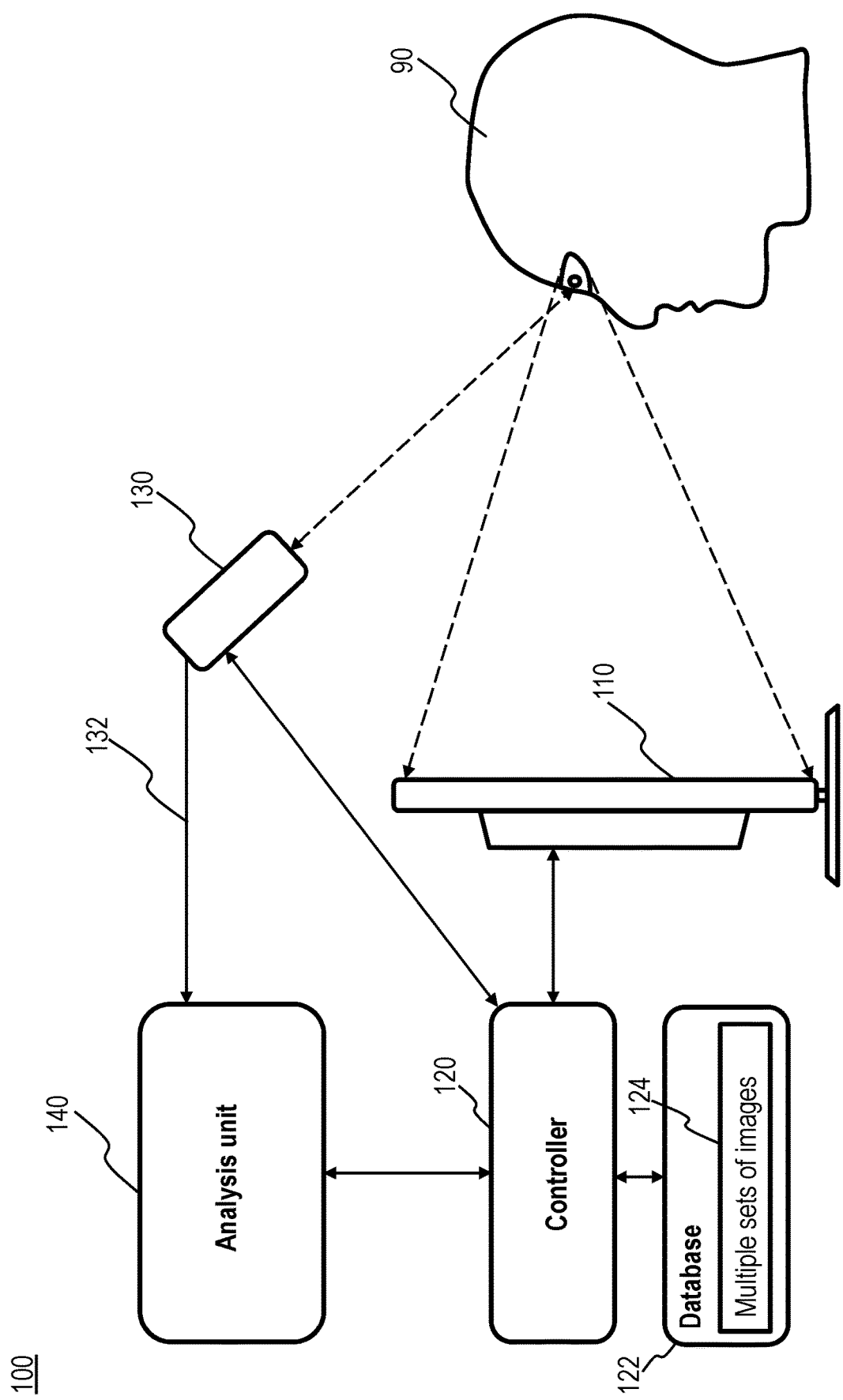
FIG. 1 is a schematic illustration of a system for analyzing involuntary eye movements of a human subject in response to a masked visual stimulating content, according to some embodiments of the invention.

It will be appreciated that, for simplicity and clarity of illustration, elements shown in the figures have not neces-

DETAILED DESCRIPTION OF THE INVENTION

In the following description, various aspects of the present invention are described. For purposes of explanation, specific configurations and details are set forth in order to provide a thorough understanding of the present invention. However, it will also be apparent to one skilled in the art that the present invention can be practiced without the specific details presented herein. Furthermore, well known features can have been omitted or simplified in order not to obscure the present invention. With specific reference to the drawings, it is stressed that the particulars shown are by way of example and for purposes of illustrative discussion of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention can be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments that can be practiced or carried out in various ways as well as to combinations of the disclosed embodiments. Also, it is to be understood that the phraseology and terminology employed herein is for the purpose of description and should not be regarded as limiting.

Unless specifically stated otherwise, as apparent from the following discussions, it is appreciated that throughout the specification discussions utilizing terms such as "processing", "computing", "calculating", "determining", "enhancing" or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices. Any of the disclosed modules or units can be at least partially implemented by a computer processor.

Generally, a method and a system for analyzing involuntary eye movements of a human subject, responsive to a masked visual content exhibiting subconscious, or on the verge of consciousness, visual stimulus are disclosed. The system may include means for presenting to a human subject visual content, possibly a video footage, in which some visual stimulus is embedded. While most of the video footage is ordinary, calm, and non-stimulating, the visual stimulating portions are contextually related to objects and topics with whom the human subject has some form of relationship on a cognitive or sentiment level. The generation of the combined video footage is such that the stimulus is briefly presented and masked by the following video footage. The duration of the stimulus is made sufficiently long to invoke a neural response beyond a specified threshold that generates respective ocular effect and alteration in a pattern of involuntary eye movements, and sufficiently short to prevent a controlled eye movement by the human subject. Since different human subjects may behave differently, the system may use a learning phase hidden to the human subject in which the effect of known stimuli on the pattern of the involuntary eye movements induced by the stimuli may be extracted. Once measured, the involuntary eye movements are analyzed in view of the respective stimulating portions—most notably their timing and their context, to yield an analysis of the human subject relationship or sentiment towards the objects presented in the visual stimulating portions.

Reference is now made to FIG. 1, which is a schematic illustration of a system 100 for analyzing involuntary eye movements of a human subject 90 in response to a masked visual stimulating content, according to some embodiments of the invention.

System 100 may include a display 110 and a database 122 in association with a controller 120. Database 122 may include multiple sets 124 of images. Controller 120 may be arranged to display (e.g., repeatedly and/or randomly), on display 110, at least some sets of images of multiple sets 124 of images. In some embodiments, at least one image in at least one set of images of multiple sets 124 of images includes a visual stimulating content masked by at least one additional image. The visual stimulating content thereof may be related (e.g., contextually or directly) to human subject 90 (e.g., as described below with respect to FIGS. 2A-2D).

System 100 may include an eye tracking unit 130. Eye tracking unit 130 may be arranged to track eye movements of a human subject 90 watching multiple sets 124 of images being displayed on display 110 and to generate corresponding multiple eye movements signals 132. For example, eye tracking unit 132 may generate at least one eye movements signal for each set of images of multiple sets 124 of images.

In some embodiments, the eye movements signals include information concerning involuntary eye movements (e.g., micro-saccades). In various embodiments, the eye movements signals include information concerning at least one of eye drift, eye blink and/or pupil's size.

System 100 may include an analysis unit 140. Analysis unit 140 may be arranged to receive eye movements signals 132 from eye tracking unit 130. Analysis unit 140 may be arranged to determine, based on multiple eye movements signals 132 and a predetermined reference dataset, a difference between at least one eye movements signal of multiple eye movements signals and other eye movements signals of multiple eye movements signals 132 (e.g., as described below with respect to FIGS. 3A-3D). In various embodiments, the difference thereof is due to a subconscious response or a response of a verge of consciousness of human subject 90 to the visual stimulating content presented in the at least one image of the corresponding at least one set of images of multiple sets of images 124.

In some embodiments, the predetermined reference dataset includes an alteration pattern in eye movements signals in response to the visual stimulating content (e.g., as described below with respect to FIG. 3B-3D). In some embodiments, the reference dataset is determined, e.g., by analysis unit 140, prior to actual testing of human subject 90 based on, for example, predetermined learning sets of images stored in database 122 (e.g., as described below with respect to FIG. 3A).

In some embodiments, multiple sets 124 of images are transmitted (e.g., by analysis unit 140) and further presented on, for example, a remote device (e.g., a smartphone) being used by human subject 90. The respective eye movements of human subject 90 may be tracked using, for example, the remote device's camera and corresponding eye movements signals may be further transmitted to, for example, analysis unit 140 for further analysis.

Reference is now made to FIGS. 2A-2D, which are graphs of various configurations of multiple sets 124 of images being displayed on a display of a system 100 for analyzing involuntary eye movements of a human subject 90 in response to a masked visual stimulating content, according to some embodiments of the invention.

FIGS. 2A-2D shows three sets of images of multiple sets of images, e.g., a first set 124-1 of images, a second set 124-2 of images and a third set 124-3 of images, being subsequently displayed on, for example, display 110 of system 100. It is noted that multiple sets 124 of images may include any number of sets (e.g., rather than three).

In some embodiments, each set of images of multiple sets 124 of images includes a first image 124a and at least one additional image, for example a second image 124b (e.g., as shown in FIG. 2A). At least one first image 124a of corresponding at least one set of images of multiple sets of images 124 may include a visual stimulating content. The visual stimulating content may be, for example, contextually and/or directly related to objects, topics and/or persons with whom/which human subject 90 has some form of relationship. The relationship thereof may be, for example, on a cognitive and/or sentiment level. Second images 124b of multiple sets of images 124 may include, for example, calm, non-stimulating and/or non-uniform content.

For example, first image 124a-2 of second set 124-2 of images may present a visual stimulating content (e.g., as indicated by the black filled first image 124a-2 peek in FIGS. 2A-2D), while first image 124a-1 and first image 124a-3 (e.g., indicated by unfilled first image 124a-1, 124a-3 peeks in FIGS. 2A-2D) of first set 124-1 of images and third set 124-3 of images, respectively, may present any non-stimulating content. In some embodiments, the visual stimulating content presented in, for example, stimulating first image 124a-2 of second set 124-2 of images and the content presented in non-stimulating first images 124a-1, 124a-3 of first and third sets 124-1, 124-3 of images, respectively, are of the same content type. For example, stimulating first image 124a-2 may present a portrait of a subject with whom human subject 90 has some form of relationship (e.g., on a cognitive and/or sentiment level) while non-stimulating first images 124a-1, 124a-3 may present portraits of subjects with whom human subject 90 has no relationship.

Controller 120 may be arranged to briefly display (e.g., on display 110) first image 124a of each set of images of multiple sets 124 of images and further mask the respective set's first image 124a by displaying the respective set's at least one additional image, e.g., second image 124b. For example, controller 120 may be arranged to display (e.g., on display 110) first image 124a of each set of images of multiple sets 124 of images during a first predetermined time duration $\Delta t_1$, and further to display, at a first predetermined time offset $\Delta t_{1\text{-}2}$ with respect to the respective set's first image 124a, the respective set's second image 124b for a second predetermined time duration $\Delta t_2$ (e.g., as shown in FIG. 2A).

The first time duration $\Delta t_1$ to display first images 124a of multiple sets 124 of images may be determined to be sufficiently long to, for example, invoke a neural response beyond a specified neural response threshold that may generate respective alteration in a pattern of involuntary eye movements of human subject 90 watching the respective set of images of multiple sets 124 of images, and yet sufficiently short to, for example, prevent a controlled eye movement by the human subject. In various embodiments, the first time duration $\Delta t_1$ ranges between 5 and 15 millisecond, the second time duration $\Delta t_1$ ranges between 50 and 150 milliseconds and/or the first time offset $\Delta t_{1\text{-}2}$ ranges between 40 and 100 milliseconds. In various embodiments, the first time duration $\Delta t_1$ is 10 milliseconds, the second time duration $\Delta t_2$ is 100 milliseconds and/or the first time offset $\Delta t_{1\text{-}2}$ is 70 milliseconds.

Controller 120 may be arranged to display (e.g., on display 110) first images 124a of each two subsequent sets of images (e.g., first set 124-1 of images and second set 124-2 of images or second set 124-2 of images and third set 124-3 of images) of multiple sets 124 of images at a second predetermined time offset $\Delta t_{1\text{-}1}$ with respect to each other (e.g., as shown in FIGS. 2A-2D). In some embodiments, the second time offset $\Delta t_{1\text{-}1}$ ranges between 0.5 and 1.5 seconds. In some embodiments, the second time offset $\Delta t_{1\text{-}1}$ is 1 second.

In some embodiments, the at least one additional image of each set of images of multiple sets of images 124 further includes a third image 124c (e.g., as shown in FIG. 2B). Third image 124c of each set of images of multiple sets of images 124 may include calm, non-stimulating content, and may be arranged to further mask the respective set's first image 124a by displaying the respective set's third image 124c after the respective set's second image 124b (e.g., as shown in FIG. 2B).

In some embodiments, controller 120 is arranged to display first image 124a of each set of images of multiple sets of images 124 during first predetermined time duration $\Delta t_1$, to further display, at first predetermined time offset $\Delta t_{1\text{-}2}$ with respect to the respective set's first image 124a, the respective set's second image 124b for second predetermined time duration $\Delta t_2$; and to further display, at a second predetermined time offset $\Delta t_{2\text{-}3}$ with respect to the respective set's second image 124b, the respective set's third image 124c for a third predetermined time duration $\Delta t_3$.

Figure 2C:
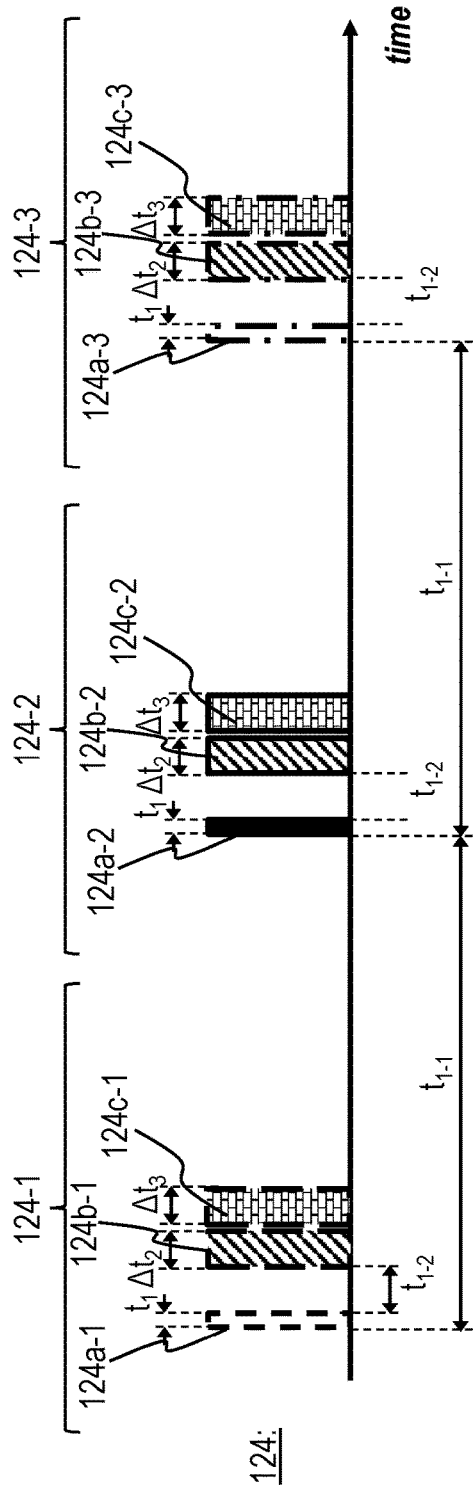

In some embodiments, the second predetermined time offset $\Delta t_{2\text{-}3}$ is set to zero (e.g., as shown in FIG. 2C). In various embodiments, the second predetermined time duration $\Delta t_2$ and/or the third predetermined time duration $\Delta t_3$ ranges between 25 and 75 milliseconds. In various embodiments, the second predetermined time duration $\Delta t_2$ is 50 milliseconds and/or the third predetermined time duration $\Delta t_3$ is 50 milliseconds.

Figure 2D:
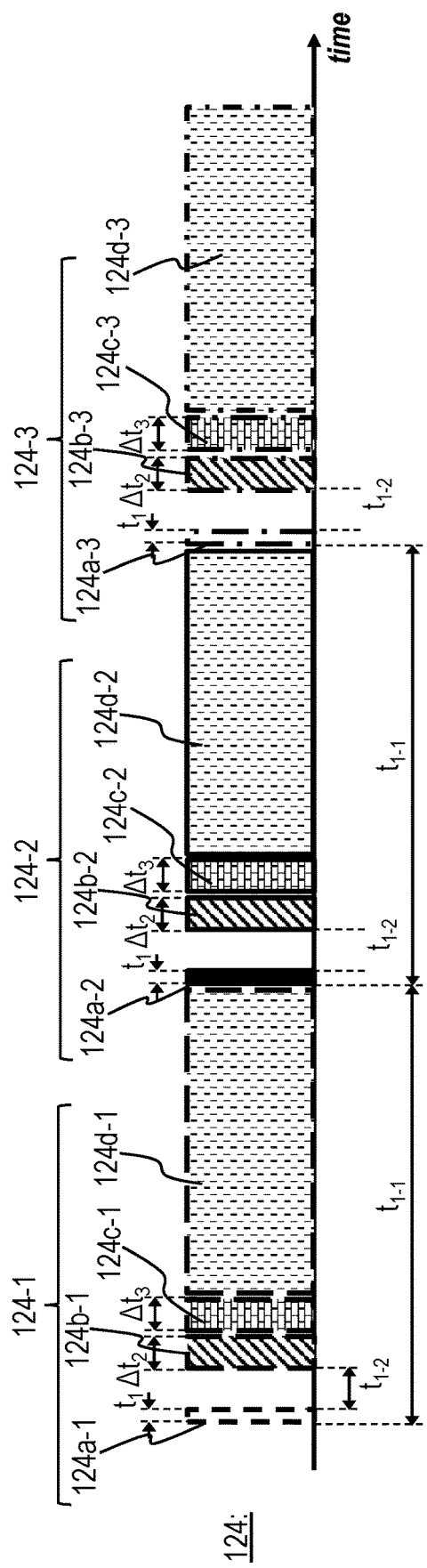

In some embodiments, the at least one additional set of images of each set of images of multiple sets 124 of images further includes a fourth image 124d (e.g., as shown in FIG. 2D). Fourth image 124d of each set of images of multiple sets 124 of images may include minimal visual content arranged to fixate human subject's 90 gaze on display 110. For example, each fourth images 124d of multiple sets 124 of images may include a black screen with a white circle in a center portion of the image thereof. In some embodiments, controller 120 is arranged to display fourth image 124d of each set of images of multiple sets of images 124, just after the respective set's third image and just before displaying first image 124a of the subsequent set of images of multiple sets of images 124 (e.g., as shown in FIG. 2D).

In some embodiments, controller 120 is arranged to repeatedly display multiple sets 124 of images on display 110. For example, controller 120 may be arranged to display first set 124-1 of images after completing the display of third set 124-3 of images. In some embodiments, controller 120 is arranged to randomly display multiple sets 124 of images on display 110. For example, controller 120 may randomly display stimulating sets of images of multiple sets 124 of images (e.g., sets of images in which the respective sets' first images include visual stimulating content(s), e.g., set 124-2) among other non-stimulating sets of images of multiple sets 124 of images.

Figure 3A:
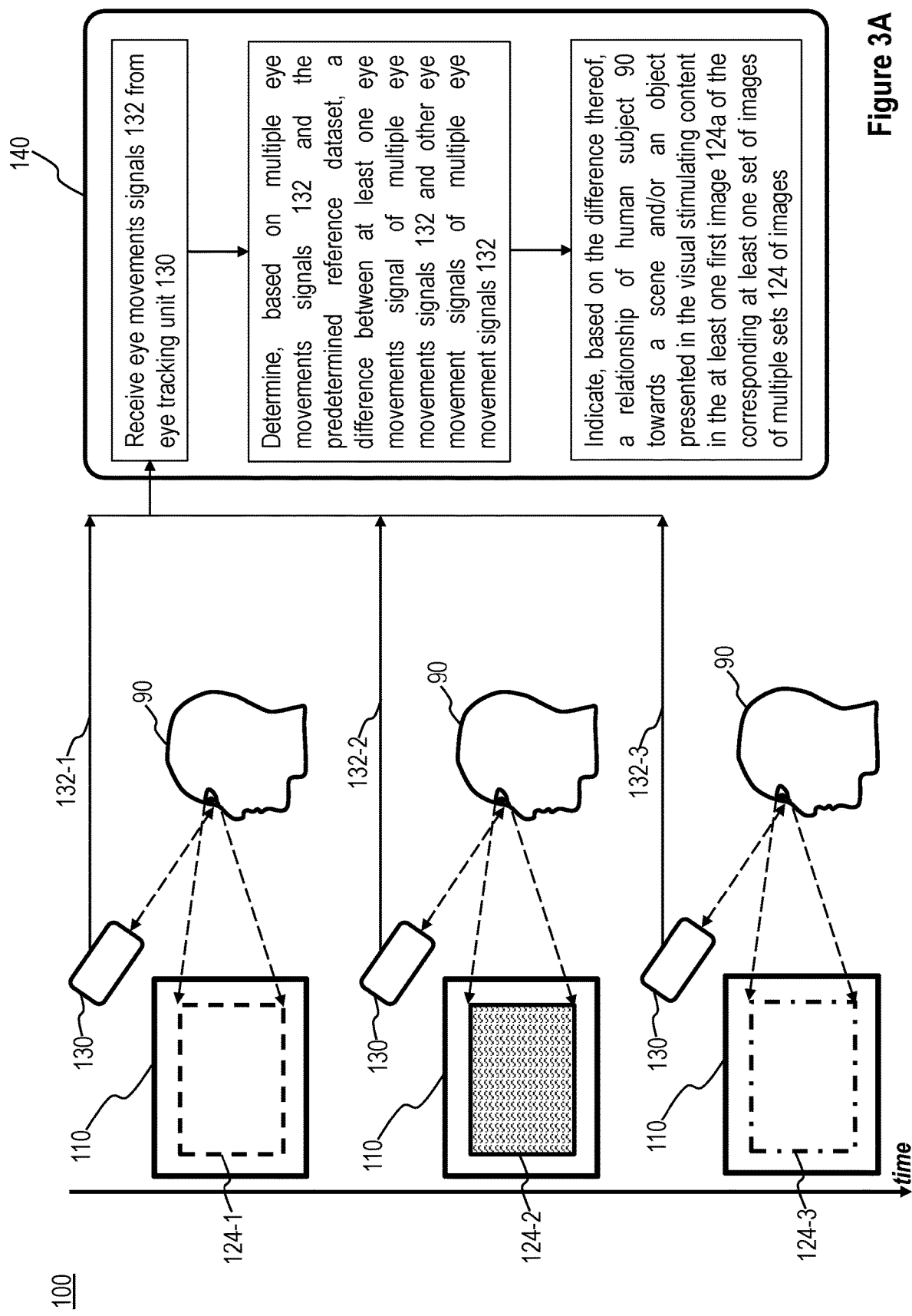
FIG. 3A is a schematic illustration of functions performed by an eye tracking unit and an analysis unit of a system for analyzing involuntary eye movements of a human subject in response to a masked visual stimulating content, according to some embodiments of the invention.

Reference is now made to FIG. 3A, which is a schematic illustration of functions performed by an eye tracking unit 130 and an analysis unit 140 of a system 100 for analyzing involuntary eye movements of a human subject 90 in response to a masked visual stimulating content, according to some embodiments of the invention.

Eye tracking unit 130 may be arranged to generate, for each set of images of multiple sets 124 of images, an eye movements signal to thereby yield multiple eye movements signals 132 (e.g., as described above with respect to FIG. 1). The multiple eye movements signals 132 may be generated by eye tracking unit 130 based on tracked eye movements of human subject 90 watching corresponding multiple sets 124 of images being displayed on display 110 (e.g., as described above with respect to FIG. 1).

For example, eye tracking unit 130 may generate a first eye movements signal 132-1 that corresponds to first set 124-1 of images of multiple sets 124 of images, a second eye movements signal 132-2 that corresponds to second set 124-2 of images of multiple sets 124 of images and/or a third eye movements signal 132-3 that corresponds to first set 124-3 of images of multiple sets 124 of images.

In some embodiments, each eye movements signal of multiple eye movements signals 132 includes information concerning involuntary eye movements (e.g., micro-saccades). In various embodiments, each eye movements signal of multiple eye movements signals 132 includes information concerning at least one of eye drift, eye blink and/or pupil's size.

It is noted that each set of images shown in FIG. 3A (e.g., first set 124-1 of images, second set 124-2 of images and third set 124-3 of images) may be identical to one of the sets of images discussed above with respect to FIGS. 2A-2D.

In some embodiments, at least one set of images of the multiple sets of images includes the visual stimulating content. Referring to FIG. 3A as example, second set 124-2 of images may include a visual stimulating content (e.g., as indicated by a patterned fill in FIG. 3A) while first set 124-1 of images and third set 124-3 of images do not include any stimulating content.

Analysis unit 140 may be arranged to receive, from eye tracking unit 130, multiple eye movements signals 132 generated by eye tracking unit 130 based on tracked eye movements of human subject 90 watching multiple sets 124 of images being displayed on display 110 (e.g., as shown in FIG. 3A).

In some embodiments, controller 120 is arranged to repeatedly display multiple sets 124 of images, such that each eye movements signal of multiple eye movements signals 132 may be generated (e.g., by analysis unit 140) by averaging the respective eye movements signals of multiple eye movements signals 132 that correspond to the respective set of images of multiple sets of images 124.

Analysis unit 140 may be further arranged to determine, based on multiple eye movements signals 132 and the predetermined reference dataset, a difference between at least one eye movements signal of multiple eye movements signals 132 and other eye movements signals of multiple eye movements signals 132.

The difference between at least one eye movements signal of multiple eye movements signals 132 and other eye movements signals of multiple eye movements signals 132 may be in response to, for example, a subconscious response or a response on a verge of consciousness of human subject 90 to the visual stimulating content presented in the at least one image of the corresponding at least one set of images of multiple sets of images 124 (e.g., as described above with respect to FIGS. 2A-2D). In some embodiments, analysis unit 140 is arranged to indicate, based on the difference thereof, a relationship of human subject 90 towards a scene and/or an object presented in the visual stimulating content in the at least one first image 124a of the corresponding at least one set of images of multiple sets 124 of images.

In some embodiments, analysis unit 140 is further arranged to determine that the difference between at least one eye movements signal of multiple eye movements signals 132 and other eye movements signals of multiple eye movements signals 132 is above a predetermined difference threshold to thereby indicate the relationship of human subject 90 towards the visual stimulating content. For example, some non-stimulating content (e.g., enhanced content) embedded in non-stimulating sets of images of multiple sets of images 124 may lead to a random eye movements response that may be similar (but not identical) to the subconscious eye movements response (or a response on a verge of consciousness) of human subject 90 to the visual stimulating content. Accordingly, the difference threshold may be predetermined to control the indication whether the difference thereof is due to the random response that is similar to the subconscious eye movements response or is due to the actual subconscious eye movements response. In various embodiments, the difference threshold may be adjusted according to desired specificity value and/or sensitivity value of system 100 (e.g., as described below).

Such a response to the visual stimulating content (e.g., the difference thereof in the eye movements signals) may vary among human subjects (e.g., as described below with respect to FIGS. 3B-3D). Since different human subjects may respond differently to the visual stimulating content, system 100 may be arranged to perform a learning phase to determine an alteration pattern in eye movements signals for each human subject 90 undergoing the testing by system 100. In some embodiments, the learning phase is hidden from human subject 90.

For example, database 122 may include learning sets of images. The learning sets of images may be displayed by controller 120 on display 110 prior to actual testing of human subject 90. The learning sets of images may be similar to multiple sets 124 of images (e.g., as described above with respect to FIGS. 2A-2D), while the visual stimulating content presented in at least one first image of corresponding at least one learning set of images of the learning sets of images may include well-known content, for example, portraits of famous people. Eye tracking unit 130 may be further arranged to track eye movements (e.g., involuntary eye movements such as micro-saccades) of human subject 90 during watching of the learning sets of images being displayed on the display 110 to thereby generate learning eye movements signals. Analysis unit 140 may be further arranged to receive the learning eye movements signals from eye tracking unit 130 and further to determine, based on the learning eye movements signals thereof, the reference dataset that includes an alternation alteration pattern in involuntary eye movements signals in response to the visual stimulating content.

In some embodiments, controller 120 is arranged to repeatedly display multiple sets 124 of images on display 110. For example, controller 120 may be arranged to display first set 124-1 of images after completing the display of third set 124-3 of images. Repeated display of multiple sets 124 of images may enable, for example, increasing the accuracy of system 100 (e.g., the ability of system 100 to indicate the relationship of the human subject towards the visual stimulating content). In some embodiments, the accuracy of system 100 ranges between 60% and 100%.

In some embodiments, multiple sets 124 of images include more than one stimulating set of images (e.g., two, three or any other number of stimulating sets of images) with different visual stimulating contents embedded therein. In some embodiments, all of the different visual stimulating contents have some form of relationship towards human subject 90 undergoing the test. In some embodiments, all of the different visual stimulating contents are related to a specific object and/or event. For example, the different stimulating visual contents may be a portrait of a specific person, a name of the specific person and/or a city in which the specific person is located. In some embodiments, embedding two or more stimulating sets of images (e.g., sets of images in which the respective sets' first images include visual stimulating content) within multiple sets 124 of images increases the accuracy of system 100 (e.g., the ability of system 100 to indicate the relationship of the human subject towards the visual stimulating content(s)).

In some embodiments, the accuracy of system 100 (e.g., the ability to indicate the relationship of the human subject towards the visual stimulating content) having single stimulating set of images of multiple sets 124 of images ranges between 60% and 80%. In some embodiments, the accuracy of system 100 having three or more stimulating sets of images of multiple sets 124 of images ranges between 85% and 100%.

In some embodiments, for a predetermined sensitivity value of 85% (e.g., 85% of true positive indications thereof), the accuracy of system 100 is 100% and the specificity is 100% (e.g., 100% of true negative indications thereof). In some embodiments, for a predetermined sensitivity value of 90%, the accuracy of system 100 is 100% and the specificity is 71%.

In some embodiments, controller 120 is arranged to randomly display multiple sets 124 of images on display 110. For example, controller 120 may randomly display stimulating sets of images of multiple sets 124 of images (e.g., sets of images in which the respective sets' first images include visual stimulating content(s), e.g., set 124-2) among other non-stimulating sets of images of multiple sets 124 of images.

Figure 3D:
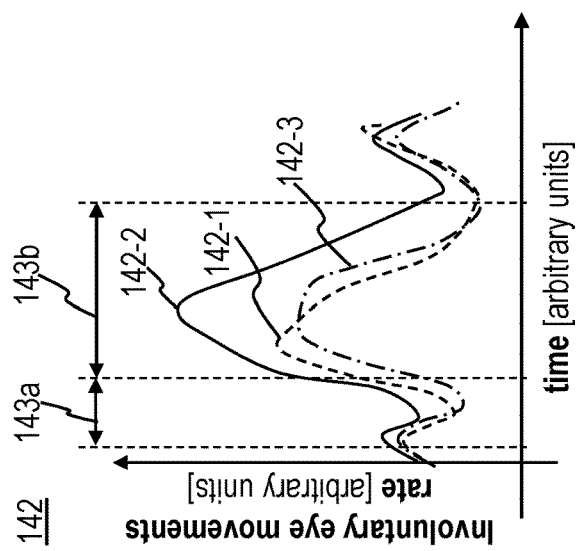
FIGS. 3B-3D are graphs showing various patterns of involuntary eye movements rates of a human subject watching multiple sets of images, determined by an analysis unit of a system for analyzing involuntary eye movements of human subject in response to a masked visual stimulating content, according to some embodiments of the invention.
Figure 3C:
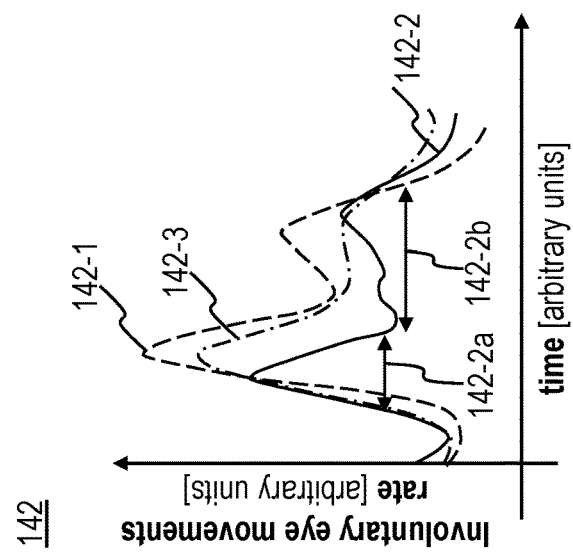
Figure 3B:
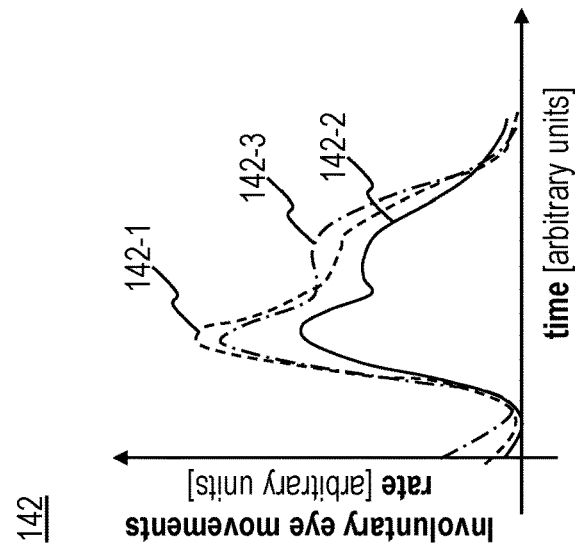

Reference is now made to FIGS. 3B-3D, which are graphs showing various patterns of involuntary eye movements rates of a human subject 90 watching multiple sets 124 of images, determined by an analysis unit 140 of a system 100 for analyzing eye movements of human subject 90 in response to a masked visual stimulating content, according to some embodiments of the invention.

Analysis unit 140 may be further arranged to determine, based on multiple eye movements signals 132, corresponding multiple datasets 142. Each dataset of multiple datasets 142 may be determined based on one eye movements signal of multiple eye movements signals 132 that correspond to respective set of images of multiple sets 124 of images.

Referring to FIG. 3A as example, analysis unit 140 may determine a first dataset 142-1 based on first eye movements signal 132-1 that corresponds to first set 124-1 of images, a second dataset 142-2 based on second eye movements signal 132-2 that corresponds to second set 124-2 of images and/or a third dataset 142-3 based on third eye movements signal 132-3 that corresponds to third set 124-3 of images.

In some embodiments, each dataset of multiple datasets 142 includes variation of involuntary eye movements rate (e.g., micro-saccades rate) of human subject 90 during watching of the corresponding set of images of multiple sets 124 of images (e.g., as described below with respect to FIGS. 3B-3D).

In some embodiments, at least one dataset of multiple datasets 142 that corresponds to the at least one set of images of multiple sets 124 of images that includes the visual stimulating content differs from other datasets of multiple datasets 142 that correspond to sets of images of multiple sets 124 of images that do not include the visual stimulating content thereof (e.g., as described below with respect to FIGS. 3B-3D).

Such a response to the visual stimulating content (e.g., an alteration in involuntary eye movements rate variation) may vary among human subjects. Some human subjects may experience significant involuntary eye movements inhibition (e.g., micro-saccades inhibition) in response to the visual stimulating content. For example, FIG. 3B shows that involuntary eye movements rate of second dataset 142-2 that corresponds to second set 124-2 of images that includes the visual stimulating content is significantly lower as compared to involuntary eye movements rates of first and third datasets 142-1, 142-3 that correspond to first and third sets 124-1, 124-3 of images, respectively, that do not include the stimulating content.

Other human subjects may experience significant involuntary eye movements (e.g., micro-saccades) in response to the visual stimulating content that may be followed by an involuntary eye movements inhibition. For example, FIG. 3C shows a region 142-2a in second dataset 142-2 (that corresponds to second set 124-2 of images that includes the visual stimulating content) in which the involuntary eye movements rate is significantly higher as compared to a subsequent region 142-2b in second dataset 142-2, which is characterized by the involuntary eye movements inhibition.

Other human subject may experience significant acceleration in involuntary eye movements (e.g., micro-saccades) in response to the visual stimulating content. For example, FIG. 3D shows that involuntary eye movements rate of second dataset 142-2 that corresponds to second set 124-2 of images that includes the visual stimulating content is significantly higher as compared to involuntary eye movements rates of first and third datasets 142-1, 142-3 that correspond to first and third sets 124-1, 124-3 of images, respectively, that do not include the visual stimulating content.

It is noted that other alteration patterns in in involuntary eye movements rate variation are also possible.

Analysis unit 140 may be further arranged to determine, based on the learning eye movements signals (e.g., as described above with respect to FIG. 3A), learning datasets including involuntary eye movements rate variations (e.g., micro-saccades rate variations) of human subject 90 during watching of multiple sets 124 of images, and further to determine, based on the learning datasets thereof, the reference dataset that includes an alteration pattern in involuntary eye movements rate variations in response to the visual stimulating content (e.g., as described above with respect to FIGS. 3B-3D).

Analysis unit 140 may be further arranged to determine, based on the multiple datasets 142 (e.g., determined based on one eye movements signal of multiple eye movements signals 132 corresponding to respective set of images of multiple sets 124 of images) and based on the predetermined reference dataset, a difference between at least one dataset of multiple datasets 142 and other datasets of multiple datasets 142. For example, referring to FIG. 3A as example, analysis unit 140 may determine, based on the multiple datasets 142 and based on the predetermined reference dataset, a difference between dataset 142-2 that corresponds to stimulating set of images 124-2 and datasets 142-1, 142-3 that correspond to non-stimulating sets of images 124-1, 124-3, respectively.

In some embodiments, analysis unit 142 is arranged to analyze, separately, at least two predetermined regions in multiple datasets 142 to thereby determine, based on the analysis thereof, differences between at least one dataset of multiple datasets 142 and other datasets of multiple datasets 142 in each of the at least two predetermined regions thereof. For example, analysis unit 140 may be arranged to compare multiple datasets 142 in a first predetermined region 143a ranging, for example, between 50 and 250 milliseconds from the onset and further to compare multiple datasets 142 in a second predetermined region 143b ranging, for example, between 250 and 800 milliseconds from the onset (e.g., as shown in FIG. 3D).

Figure 4:
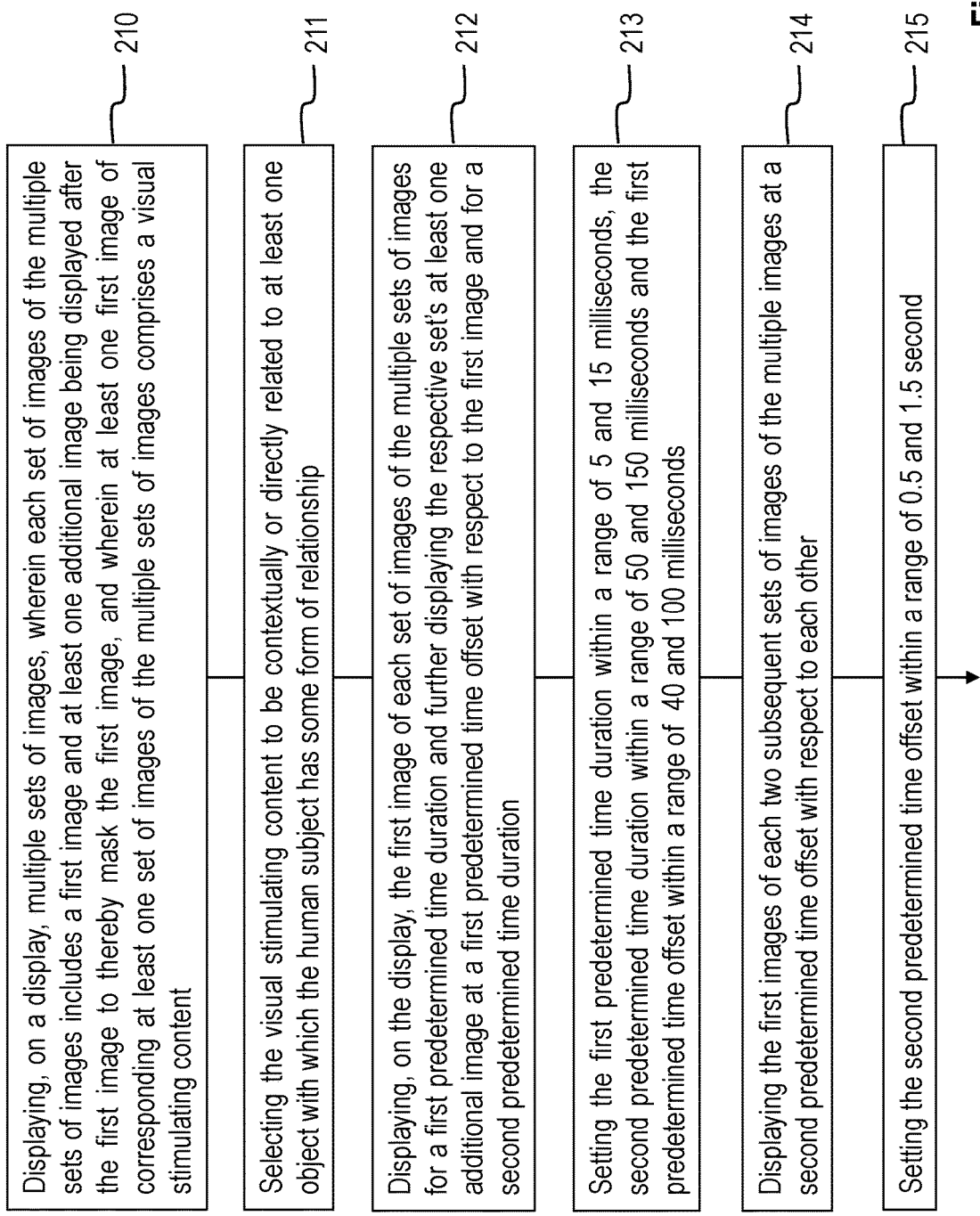
FIG. 4 is a flowchart of a method of analyzing involuntary eye movements of a human subject in response to a masked visual stimulating content, according to some embodiments of the invention.

Reference is now made to FIG. 4, which is a flowchart of a method 200 of analyzing involuntary eye movements of a human subject in response to a masked visual stimulating content, according to some embodiments of the invention. Method 200 may be utilized by, for example, system 100 that may be arranged to utilize method 200.

Method 200 may include displaying (step 210), on a display (e.g., display 110 as described above with respect to FIG. 1 and FIG. 3A), multiple sets of images, wherein each set of images of the multiple sets of images includes a first image and at least one additional image being displayed after the first image to thereby mask the first image, and wherein at least one first image of corresponding at least one set of images of the multiple sets of images comprises a visual stimulating content. In various embodiments, method 200 includes displaying the multiple sets of images thereof repeatedly and/or randomly (e.g., as described above with respect to FIGS. 2A-2D).

In some embodiments, method 200 includes selecting (step 211) the visual stimulating content to be contextually or directly related to at least one object with which the human subject has some form of relationship.

In some embodiments, method 200 includes displaying (step 212), on the display, the first image of each set of images of the multiple sets of images for a first predetermined time duration and further displaying the respective set's at least one additional image at a first predetermined time offset with respect to the first image and for a second predetermined time duration (e.g., as described above with respect to FIGS. 2A-2D). In various embodiments, method 200 includes setting (step 213) the first predetermined time duration within a range of 5 and 15 milliseconds, the second predetermined time duration within a range of 50 and 150 milliseconds and the first predetermined time offset within a range of 40 and 100 milliseconds. In various embodiments, method 200 includes setting the first predetermined time duration to 10 milliseconds, the second predetermined time duration to 100 milliseconds and the first predetermined time offset to 70 milliseconds.

In some embodiments, method 200 includes displaying (step 214) the first images of each two subsequent sets of images of the multiple images at a second predetermined time offset with respect to each other. In some embodiments, method 200 includes setting (step 215) the second predetermined time offset within a range of 0.5 and 1.5 seconds. In some embodiments, method 200 includes setting the second predetermined time offset to 1 second.

In some embodiments, method 200 includes arranging (step 216) the at least one additional image of each set of images of the multiple sets of images to include a second image and a third image, and further displaying the respective set's second image for a second predetermined time duration and displaying the respective set's third image at a second predetermined time offset with respect to the respective set's second image and for a third predetermined time duration.

In some embodiments, method 200 includes setting (step 217) the second predetermined time offset to zero, the second predetermined time duration within a range of 25 and 75 milliseconds and the third predetermined time duration within a range of 25 and 75 milliseconds. In various embodiments, method 200 includes setting the second predetermined time duration $\Delta t_2$ to 50 milliseconds and/or setting the third predetermined time duration $\Delta t_3$ to 50 milliseconds.

In some embodiments, method 200 includes arranging (step 218) the at least one additional image of each set of images of the multiple sets of images to further include a fourth image, and further displaying the respective set's fourth image just after the respective set's third image and just upon the first image of the subsequent set of images of multiple sets of images.

In various embodiments, method 200 include arranging (step 219) the second image and the third image of each set of images of the multiple sets of images to mask the respective set's first image and further arranging the respective set's fourth image to fixate a gaze of the human subject on the display.

Method 200 may include tracking (step 220), by an eye tracking unit (e.g., eye tracking unit 130 as described above with respect to FIG. 1 and FIG. 3A), involuntary eye movements (e.g., micro-saccades) of the human subject watching the multiple sets of images being displayed on the display and yielding corresponding multiple eye movements signals.

Method 200 may include receiving (step 230), by an analysis unit (e.g., analysis unit 140 as described above with respect to FIG. 1 and FIG. 3A), the multiple eye movements signals from the eye tracking unit and determining, by the analysis unit, based on the multiple eye movements signals and a predetermined reference dataset, a difference between at least one eye movements signal of the multiple eye movements signals and other eye movements signals of the multiple eye movements signals.

In some embodiments, the predetermined reference dataset includes an alteration pattern in eye movements signals of the human subject in response to the visual stimulating content (e.g., as described above with respect to FIG. 1 and FIG. 3A). In various embodiments, the difference thereof is due to a subconscious response or a response on a verge of consciousness of the human subject to the visual stimulating content presented in the corresponding at least one first image of the corresponding at least one set of images of the multiple sets of images (e.g., as described above with respect to FIG. 1 and FIG. 3A).

In some embodiments, method 200 includes determining (step 232), by the analysis unit, based on the multiple eye movements signals, corresponding multiple datasets, wherein each dataset of the multiple datasets includes an involuntary eye movements rate variation (e.g., micro-saccades rate variation) of the human subject during watching of the corresponding set of images of the multiple sets of images (e.g., as described above with respect to FIGS. 3A-3D). In some embodiments, the predetermined reference dataset includes alteration pattern in involuntary eye movements rate variations in response to the visual stimulating content (e.g., as described above with respect to FIGS. 3A-3D).

In some embodiments, method 200 includes determining (step 233), by the analysis unit, each dataset of the multiple datasets based on one eye movements signal of the multiple eye movements signals corresponding to respective set of images of the multiple sets of images.

In some embodiments, method 200 include repeatedly displaying (stage 234), on the display, the multiple sets of images, and further determining, by the analysis unit, each dataset of the multiple datasets by averaging the respective eye movements signals of the multiple eye movements signals that correspond to the respective set of images of the multiple sets of images.

In some embodiments, method 200 includes indicating (step 236), by the analysis unit, based on the difference between at least one eye movements signal of the multiple eye movements signals and other eye movements signals of the multiple eye movements signals, a relationship of the human subject towards the visual stimulating content in the at least one first image of the corresponding at least one set of images of the multiple sets of images.

In some embodiments, method 200 includes determining (step 238) that the difference thereof is above a predetermined difference threshold to thereby indicate the relationship of the human subject towards the visual stimulating content.

Method 200 may include determining (step 240), by the analysis unit, a reference dataset prior to actual testing of the human subject. In some embodiments, method 200 includes displaying (step 242), on the display, learning sets of images prior to the actual testing of the human subject. In some embodiments, method 200 includes tracking (step 244), by the eye tracking unit, involuntary eye movements (e.g., micro-saccades) of the human subject during watching of the learning sets of images being displayed on the display and generating learning eye movements signals.

In some embodiments, method 200 includes receiving (step 246), by the analysis unit, the learning eye movements signals from the eye tracking unit and further determining, by the analysis unit, based on the learning eye movements signals thereof, the reference dataset.

In some embodiments, method 200 includes determining (step 248), by the analysis unit, based on the learning eye movements signals, learning datasets including involuntary eye movements rate variations (e.g., micro-saccades rate variations) of the human subject during watching of the multiple sets of images, and further determining, based on the learning datasets thereof, the reference dataset that includes an alteration pattern in involuntary eye movements rate variations in response to the visual stimulating content (e.g., as described above with respect to FIGS. 3B-3D).

In some embodiments, method 200 includes at least one of repeatedly and randomly displaying (step 250), on the display, the multiple sets of images.

Advantageously, the disclosed systems and methods may provide noninvasive and robust tool for indicating the relationship of the human subject to the visual stimulating content embedded within, for example, a video footage. Advantageously, presenting the visual stimulating content for a predetermined time duration that is: (i) sufficiently long to invoke, for example, a neural response beyond a specified threshold that generates respective ocular effect and alteration in a pattern of involuntary eye movements; and (ii) sufficiently short to prevent a controlled eye movement by the human subject; and further masking the visual stimulating content thereof by, for example, ordinary, calm, and/or non-stimulating content may enable detection of a subconscious response or a response on a verge of consciousness of the human subject towards objects and/or events related to the visual stimulating content thereof. Advantageously, the sensitivity of the disclosed systems and methods to indicate the relationship of the human subject towards the visual stimulating content ranges between 85% and 100%.

Aspects of the present invention are described above with reference to flowchart illustrations and/or portion diagrams of methods, apparatus (systems) and computer program products according to embodiments of the invention. It will be understood that each portion of the flowchart illustrations and/or portion diagrams, and combinations of portions in the flowchart illustrations and/or portion diagrams, can be implemented by computer program instructions. These computer program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or portion diagram or portions thereof.

These computer program instructions can also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or portion diagram portion or portions thereof. The computer program instructions can also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or portion diagram portion or portions thereof.

The aforementioned flowchart and diagrams illustrate the architecture, functionality, and operation of possible implementations of systems, methods and computer program products according to various embodiments of the present invention. In this regard, each portion in the flowchart or portion diagrams can represent a module, segment, or portion of code, which includes one or more executable instructions for implementing the specified logical function(s). It should also be noted that, in some alternative implementations, the functions noted in the portion can occur out of the order noted in the figures. For example, two portions shown in succession can, in fact, be executed substantially concurrently, or the portions can sometimes be executed in the reverse order, depending upon the functionality involved. It will also be noted that each portion of the portion diagrams and/or flowchart illustration, and combinations of portions in the portion diagrams and/or flowchart illustration, can be implemented by special purpose hardware-based systems that perform the specified functions or acts, or combinations of special purpose hardware and computer instructions.

In the above description, an embodiment is an example or implementation of the invention. The various appearances of "one embodiment", "an embodiment", "certain embodiments" or "some embodiments" do not necessarily all refer to the same embodiments. Although various features of the invention can be described in the context of a single embodiment, the features can also be provided separately or in any suitable combination. Conversely, although the invention can be described herein in the context of separate embodiments for clarity, the invention can also be implemented in a single embodiment. Certain embodiments of the invention can include features from different embodiments disclosed above, and certain embodiments can incorporate elements from other embodiments disclosed above. The disclosure of elements of the invention in the context of a specific embodiment is not to be taken as limiting their use in the specific embodiment alone. Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described. Meanings of technical and scientific terms used herein are to be commonly understood as by one of ordinary skill in the art to which the invention belongs, unless otherwise defined. While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A system for analyzing involuntary eye movements of a human subject in response to a masked visual stimulating content, the system comprising:
   a display;
   a database comprising multiple sets of images, wherein each set of images of the multiple sets of images comprises a first image and at least one additional image displayed after the respective set's first image to thereby mask the respective set's first image, and wherein the first image of at least one set of images of the multiple sets of images comprises a visual stimulating content;
   a controller in association with the display and with the database, the controller is arranged to display, on the display, the multiple sets of images such that:
      the first image of each set of images of the multiple sets of images is displayed for a first predetermined time duration, wherein the first predetermined time duration ranges between 5 and 15 milliseconds;
      the at least one additional image of each set of images of the multiple sets of images is displayed for a second predetermined time duration and at a first predetermined time offset with respect to the first image of the respective set of images, wherein the second predetermined time duration ranges between 50 and 150 milliseconds and the first predetermined time offset ranges between 40 and 100 milliseconds; and
      the first images of each two sequential sets of images of the multiple sets of images are displayed at a second predetermined time offset with respect to each other, wherein the second predetermined time offset ranges between 0.5 and 1.5 seconds;
   an eye tracking unit arranged to track involuntary eye movements of the human subject watching the multiple sets of images being displayed on the display to generate corresponding multiple eye movements signals; and
   an analysis unit arranged to receive, from the eye tracking unit, the multiple eye movements signals and to determine, based on the multiple eye movements signals and a predetermined reference dataset, a difference between at least one eye movements signal of the multiple eye movements signals and other eye movements signals of the multiple eye movements signals, when the difference thereof is due to at least one of a subconscious response or a response on a verge of consciousness of the human subject to the visual stimulating content presented in the corresponding at least one first image of the corresponding at least one set of images of the multiple sets of images.

2. The system of claim 1, wherein the stimulating visual content is contextually or directly related to at least one object with which the human subject has some form of relationship.

3. The system of claim 1, wherein the predetermined reference dataset comprises an alteration pattern in eye movements signals of the human subject in response to the visual stimulating content.

4. The system of claim 1, wherein the analysis unit is further arranged to indicate, based on the difference between at least one eye movements signal of the multiple eye movements signals and other eye movements signals of the multiple eye movements signals, a relationship of the human subject towards the visual stimulating content in the at least one first image of the corresponding at least one set of images of the multiple sets of images.

5. The system of claim 4, wherein the analysis unit is further arranged to determine that the difference thereof is above a predetermined difference threshold to thereby indicate the relationship of the human subject towards the visual stimulating content.

6. The system of claim 1, wherein each set of images of the multiple sets of images comprises at least one second image, at least one third image and at least one fourth image, wherein the respective set's at least one second image and at least one third image are arranged to mask the respective set's first image and wherein the respective set's at least one fourth image is arranged to fixate a gaze of the human subject on the display.

7. The system of claim 1, wherein the controller is arranged to at least one of repeatedly and randomly display, on the display, the multiple sets of images.

8. A method of analyzing eye movements of a human subject in response to a masked visual stimulating content, the method comprising:
   displaying, on a display, multiple sets of images, wherein each set of images of the multiple sets of images comprises a first image and at least one additional image being displayed after the first image to thereby mask the first image, the first image of at least one set of images of the multiple sets of images comprises a visual stimulating content, the first image of each set of images of the multiple sets of images is displayed for a first predetermined time duration, wherein the first predetermined time duration ranges between 5 and 15 milliseconds, the at least one additional image of each set of images of the multiple sets of images is displayed for a second predetermined time duration and at a first predetermined time offset with respect to the first image of the respective set of images, wherein the second predetermined time duration ranges between 50 and 150 milliseconds and the first predetermined time offset ranges between 40 and 100 milliseconds, and the first images of each two sequential sets of images of the multiple sets of images are displayed at a second predetermined time offset with respect to each other, wherein the second predetermined time offset ranges between 0.5 and 1.5 seconds;

tracking, by an eye tracking unit, involuntary eye movements of the human subject watching the multiple sets of images being displayed on the display and generating corresponding multiple eye movements signals;

receiving, by an analysis unit, the multiple eye movements signals from the eye tracking unit and determining, by the analysis unit, based on the multiple eye movements signals and a predetermined reference dataset, a difference between at least one eye movements signal of the multiple eye movements signals and other eye movements signals of the multiple eye movements signals, when the difference thereof is due to at least one of a subconscious response or a response on a verge of consciousness of the human subject to the visual stimulating content presented in the corresponding at least one first image of the corresponding at least one set of images of the multiple sets of images.

9. The method of claim 8, further comprising selecting the visual stimulating content to be contextually or directly related to at least one object with which the human subject has some form of relationship.

10. The method of claim 8, wherein the predetermined reference dataset comprises an alteration pattern in eye movements signals in response to the visual stimulating content.

11. The method of claim 8, further comprising indicating, by the analysis unit, based on the difference, a relationship of the human subject towards the visual stimulating content in the at least one first image of the corresponding at least one set of images of the multiple sets of images.

12. The method of claim 11, further comprising determining that the difference thereof is above a predetermined difference threshold to thereby indicate the relationship of the human subject towards the visual stimulating content.

13. The method of claim 8, further comprising each set of images of the multiple sets of images to comprise at least one second image, at least one third image and at least one fourth image, and further arranging the respective set's at least one second image and at least one third image to mask the respective set's first image and the respective set's at least one fourth image to fixate a gaze of the human subject on the display.

14. The method of claim 8, further comprising at least one of repeatedly and randomly displaying, on the display, the multiple sets of images.

* * * * *